United States Patent
Hasegawa (10) Patent No.: US 10,537,296 B2
(45) Date of Patent: Jan. 21, 2020

(54) MEDICAL IMAGE DIAGNOSTIC APPARATUS

(71) Applicant: Canon Medical Systems Corporation, Otawara-shi (JP)

(72) Inventor: Takuya Hasegawa, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 159 days.

(21) Appl. No.: 15/880,654

(22) Filed: Jan. 26, 2018

(65) Prior Publication Data

US 2018/0242937 A1 Aug. 30, 2018

(30) Foreign Application Priority Data

Feb. 27, 2017 (JP) .................. 2017-035050

(51) Int. Cl.
*H05G 1/30* (2006.01)
*A61B 6/00* (2006.01)
*G01N 23/046* (2018.01)

(52) U.S. Cl.
CPC ............ *A61B 6/4435* (2013.01); *A61B 6/461* (2013.01); *A61B 6/54* (2013.01); *G01N 23/046* (2013.01); *G01N 2223/309* (2013.01); *G01N 2223/321* (2013.01)

(58) Field of Classification Search
CPC ........... A61B 6/0492; A61B 6/12; A61B 6/58; A61B 6/583; A61B 6/584; A61B 6/585
See application file for complete search history.

(56) References Cited

U.S. PATENT DOCUMENTS

| 2003/0095635 A1 | 5/2003 | Moritake et al. |
| 2006/0029181 A1* | 2/2006 | Chen .................. A61B 6/00 378/17 |
| 2017/0105691 A1* | 4/2017 | Shindo ............... A61B 6/035 |

FOREIGN PATENT DOCUMENTS

| JP | 2003-153889 | 5/2003 |
| JP | 2004-357919 | 12/2004 |

* cited by examiner

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

According to one embodiment, a medical image diagnostic apparatus includes a gantry, columns, gantry drive motors, position detectors, and gantry control circuitry. The gantry has a bore along a vertical direction. The columns movably support the gantry along the vertical direction, with one end of the bore facing a floor surface and the gantry being interposed between the columns. The gantry drive motors move the gantry along the vertical direction. The position detectors detect support positions at which the gantry is supported in each of the columns. The gantry control circuitry determines whether or not movement of the gantry along the vertical direction is possible, based on information regarding misalignment between the support positions.

9 Claims, 3 Drawing Sheets

F I G. 3

MEDICAL IMAGE DIAGNOSTIC APPARATUS

CROSS-REFERENCE TO RELATED APPLICATIONS

This application is based upon and claims the benefit of priority from the prior Japanese Patent Application No. 2017-035050, filed Feb. 27, 2017, the entire contents of which are incorporated herein by reference.

FIELD

Embodiments described herein relate generally to a medical image diagnostic apparatus.

BACKGROUND

Since a conventional whole-body X-ray computed tomography apparatus carries out imaging for a patient who lies on the bed, image analysis and dynamic observation is difficult to carry out because of the patient's own weight being applied to the patient's joints and organs. An X-ray computed tomography apparatus arranged in such a manner that its gantry is placed in parallel with the ceiling and the floor so that the gantry can be driven in a vertical direction (hereinafter, a standing-state radiography X-ray CT apparatus) is therefore clinically useful to facilitate image analysis and dynamic observation. The standing-state radiography X-ray CT apparatus can carryout imaging of a subject in a standing state or a sitting state by driving the gantry in a vertical direction. The driving of the gantry in the vertical direction is performed by synchronous control on mechanism units which are respectively provided at two columns that support the gantry from both sides thereof.

When driving the gantry in the vertical direction in the standing-state radiography X-ray CT apparatus, regardless of the synchronous control on the mechanism units provided at two columns, a misalignment which is a difference in the height of the gantry from the floor between the left and right columns may occur due to malfunction of the mechanism units or physical factors, such as an object being caught between the gantry and the column. If imaging is carried out with a significant misalignment which is caused when adjusting an imaging position, a reconstruction image will be affected by the misalignment. In such a case, imaging needs to be performed once again and an amount of X-rays to which a subject is exposed will be increased. Since the axes of the two columns are misaligned because of the misalignment, an intended operation for the gantry may not be properly carried out. In such a case, there may be harm to a subject, such as a subject being caught between the gantry and the column, or a malfunction of the apparatus. Since the gantry of the standing-state radiography X-ray CT apparatus is very heavy, a misalignment may cause serious harm.

DETAILED DESCRIPTION

In general, according to one embodiment, a medical image diagnostic apparatus includes a gantry, a plurality of columns, a plurality of gantry drive motors, a plurality of position detectors, and gantry control circuitry. The gantry has a bore along a vertical direction. The plurality of columns movably support the gantry along the vertical direction, with one end of the bore facing a floor surface and the gantry being interposed between the plurality of columns. The plurality of gantry drive motors move the gantry along the vertical direction. The plurality of position detectors detect a plurality of support positions at which the gantry is supported in each of the plurality of columns. The gantry control circuitry determines whether or not movement of the gantry along the vertical direction is possible, based on information regarding misalignment between the plurality of support positions.

In the following, the medical image diagnostic apparatus according to the present embodiment will be explained with reference to the drawings. In the description below, structural elements having substantially the same functions and configurations will be denoted by the same reference symbols, and a repetitive description of such elements will be given only where necessary. In the following, to make the description more specific, an X-ray computed tomography apparatus will be explained as an example of the medical image diagnostic apparatus of the present embodiment. The medical image diagnostic apparatus according to the present embodiment is not limited to an X-ray computed tomography apparatus, and may be a modality that is capable of obtaining an image of a subject using a gantry having a penetrated bore, such as an magnetic resonance imaging (MRI) apparatus, a positron emission tomography (PET) apparatus, a single photon emission computed tomography (SPECT) apparatus, a PET-MR apparatus, a PET-CT apparatus, a SPECT-MR apparatus, and a SPECT-CT apparatus, and the like.

Figure 1:
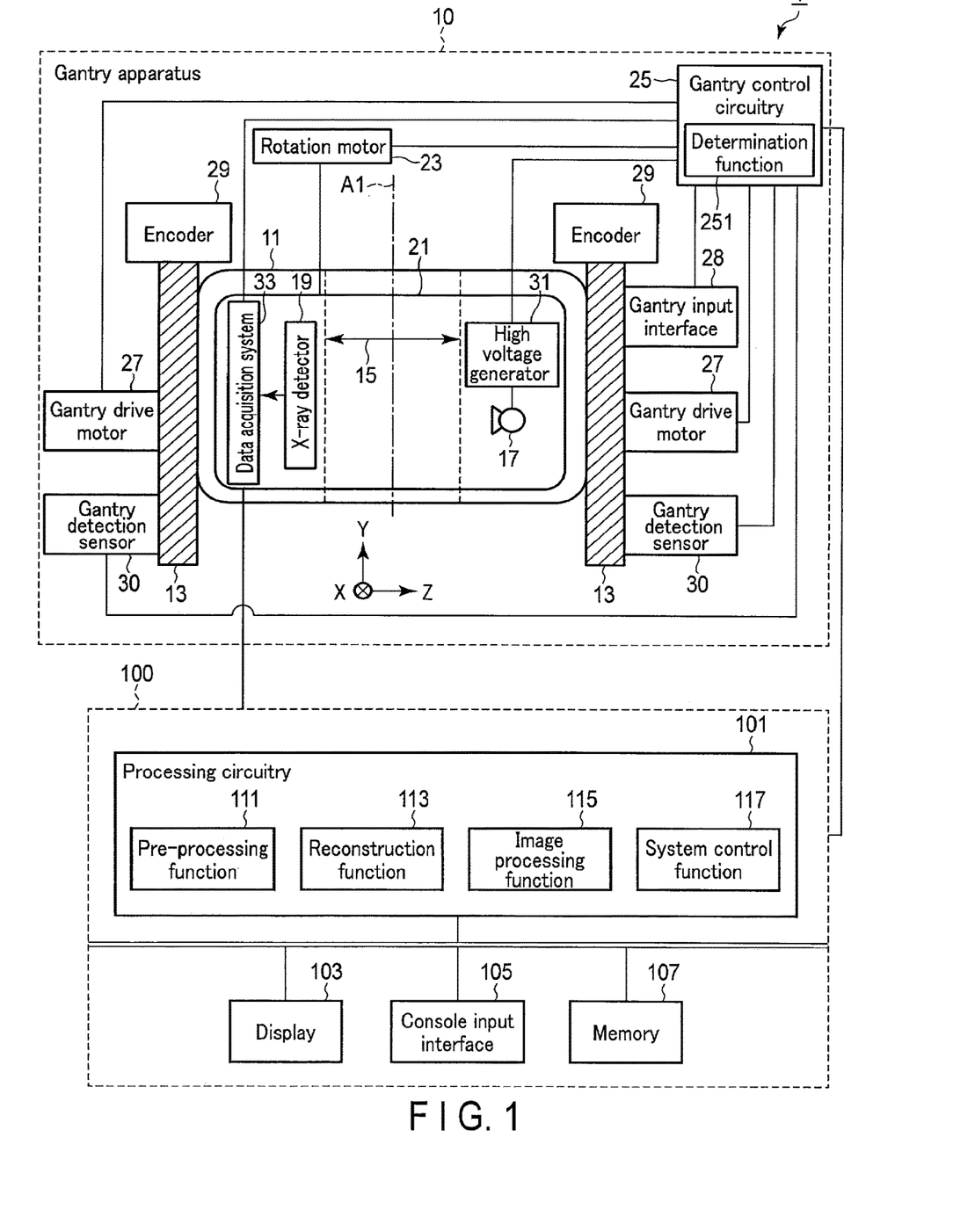
FIG. 1 is a diagram showing a configuration of an X-ray computed tomography apparatus according to the present embodiment.

FIG. 1 is a diagram showing a configuration of the X-ray computed tomography apparatus 1 according to the present embodiment. As shown in FIG. 1, the X-ray computed tomography apparatus according to the present embodiment includes a gantry apparatus 10 and a console 100. For example, the gantry apparatus 10 is installed in a CT radiography room, and the console 100 is installed in a control room adjacent to the CT radiography room. The gantry apparatus 10 and the console 100 are communicably connected to each other by wire or wirelessly. The gantry apparatus 10 is a scanning apparatus configured to perform X-ray computed tomography (referred to as X-ray CT hereinafter) for subjects in the standing and sitting positions. The console 100 has a computer for controlling the gantry 10, etc. As shown in FIG. 1, the gantry apparatus 10 includes the gantry 11, a plurality of columns 13 (a gantry supporting unit), gantry control circuitry 25 (a gantry controlling unit), gantry drive motors 27, a gantry input interface 28 (an operation panel), and position detectors (an encoder 29 and a gantry detection sensor 30).

The gantry 11 has a main frame (not shown) made of metal, such as aluminum, and a rotation frame 21 that is rotatably supported around the central axis A1 through bearings, etc. by the main frame. A slip ring (not shown) is provided at a contact portion of the main frame with the rotation frame 21. A conductive brush (not shown) is attached to the contact portion of the main frame to be brought into slidable contact with the slip ring. The rotation frame 21 is a metal frame made of, for example, aluminum, in an annular shape. An X-ray tube 17 and an X-ray detector 19 are attached to the rotation frame 21.

Upon receiving power supplied from the rotation motor 23, the rotation frame 21 rotates around the central axis A1 of the bore 15 at constant angular velocity. The rotation motor 23 generates power to rotate the rotation frame 21 under the control of the gantry control circuitry 25. More specifically, the rotation motor 23 generates power by being driven at a rotational speed corresponding to the duty ratio, etc. of a driving signal from the gantry control circuitry 25. The rotation motor 23 is achieved by a motor such as a direct drive motor and a servo motor. The rotation motor 23 is accommodated in, for example, the gantry 11.

As shown in FIG. 1, the X-ray tube 17 receives a high voltage from a high-voltage generator 31 to generate X-rays. The high-voltage generator 31 is attached to, for example, the rotation frame 21. The high voltage generator 31 generates a high voltage under the control of the gantry control circuitry 25, using electric power supplied from a power source apparatus (not shown) in the gantry apparatus 10 via the slip ring. The high voltage generator 31 and the X-ray tube 17 are electrically connected by a high voltage cable (not shown). The high voltage generated by the high-voltage generator 31 is applied to the X-ray tube 17 through the high-voltage cable.

The X-ray detector 19 detects an X-ray that is generated from the X-ray tube 17 and transmitted through a subject P. The X-ray detector 19 has a plurality of X-ray detection elements (not shown) which are arranged on a two-dimensional curved surface. Each X ray detection element converts the detected X-rays into an electrical signal having a peak value corresponding to the intensity of the X-rays. Each X-ray detection element includes, for example, a scintillator and a photoelectric converting element. The scintillator generates fluorescence by the entrance of X-rays. The photoelectric converting element converts the generated fluorescence into a charge pulse. The charge pulse has a peak value corresponding to the intensity of the generated X-rays. As the photoelectric converting element, a circuit element that converts fluorescence into electrical signals, such as a photomultiplier or a photodiode, is used. The X-ray detector 19 according to the present embodiment is not limited to an indirect-conversion type detector which converts an X-ray into fluorescence first and then into an electrical signal, but may be a direct-conversion type detector which converts an X-ray directly into an electrical signal.

A data acquisition system 33 collects digital data indicative of the intensity of X-rays decayed by the subject P for each view. The data acquisition system 33 is achieved by, for example, a semiconductor integrated circuit in which an integration circuit provided for each of the X-ray detection elements and an A/D converter are implemented in parallel. The data acquisition system 33 is connected to the X-ray detector 19 in the gantry 11. The integration circuit integrates electrical signals from the X-ray detection elements for a predetermined view period to generate integration signals. The A/D converter converts the integration signals into digital data having a data value corresponding to the peak value of the integration signals. The digital data after conversion is called raw data. The raw data is a set having a channel number and a column number of the X-ray detection elements as a data generation source, and a digital value of X-ray intensity identified by a view number indicative of an acquired view. For example, the raw data is output to the console 100 through a non-contact data transmission apparatus (not shown) stored in the gantry 11. The data acquisition system 33 (DAS) may be referred to as data acquisition circuitry.

The gantry control circuitry 25 controls the high voltage generator 31, the rotation motor 23, the gantry drive motors 27, and the data acquisition system 33, etc. in accordance with instructions from the console 100. The gantry control circuitry 25 also controls the gantry drive motors 27 in accordance with the instructions from the gantry input interface 28. The gantry control circuitry 25 achieves a determination function 251 by executing a program. The determination function 251 will be described later in detail. The gantry control circuitry 25 includes, as hardware resources, a processing apparatus (processor), such as a CPU (Central Processing Unit) or an MPU (Micro Processing Unit), and a storage device (memory), such as a ROM (Read Only Memory) or a RAM (Random Access Memory). In addition, the gantry control circuitry 25 may be achieved by an ASIC (Application Specific Integrated Circuit), an FPGA (Field Programmable Gate Array), a CPLD (Complex Programmable Logic Device), or an SPLD (Simple Programmable Logic Device). The processing apparatus achieves the function by reading and executing programs stored in the storage device. Instead of being programs stored in the storage device, programs can be incorporated directly into a circuit of the processing apparatus. In this case, the processing apparatus achieves the function by reading and executing the programs incorporated in the circuit.

As shown in FIG. 1, the console 100 includes processing circuitry 101, a display 103 (a notification section), a console input interface 105 (an input section), and a memory 107 (a memory section or a storage). Data communication between the processing circuitry 101, the display 103, the console input interface 105, and the memory 107 is performed via a bus.

The processing circuitry 101 includes, as hardware resources, a processor, such as a CPU, an MPU, or a Graphical Processing Unit (GPU), and a memory, such as a ROM or a RAM. The processing circuitry 101 executes various programs to achieve a preprocessing function 111, a reconstruction function 113, an image processing function 115, and a system control function 117.

The processing circuitry 101, which achieves the preprocessing function 111, subjects raw data transmitted from the gantry 10 to preprocessing, such as logarithmic conversion. The preprocessed raw data is referred to as projection data.

The processing circuitry 101, which achieves the reconstruction function 113, generates a CT image representing a space distribution of CT values relating to a subject based on the projection data generated by the pre-processing function 111. As the image reconstruction algorithm, a known image reconstruction algorithm, such as an FBP (Filtered Back Projection) method or a successive approximation reconstruction method, may be adopted.

The processing circuitry 101, which achieves the image processing function 115, subjects the CT image reconstructed by the reconstruction function 113 to various image processing. For example, the processing circuitry 101 subjects the CT image to three-dimensional image processing, such as volume rendering, surface volume rendering, image value projection processing, Multi-Planer Reconstruction (MPR) processing, Curved MPR (CPR) processing, etc. to generate a display image.

The processing circuitry 101, which achieves the system control function 117, integrally controls the X-ray computed tomography apparatus 1 according to the present embodiment. Specifically, the processing circuitry 101 reads a control program stored in the memory 107 and expands it in a memory, and controls the respective units of the X-ray computed tomography apparatus in accordance with the expanded control program.

The pre-processing function 111, the reconstruction function 113, the image processing function 115, and the system control function 117 may be implemented by the processing circuitry 101 on a single substrate, or may be implemented by the processing circuitry 101 on a plurality of substrates.

The display 103 displays various data, such as a two-dimensional CT image and a display image. Specifically, the display 103 converts data representing a display target into video signals, and displays the video signals representing the display target. As the display 103, for example, a CRT display, a liquid crystal display, an organic EL display, an LED display, a plasma display, or any other display known in this technical field may be used as appropriate.

The console input interface 105 accepts various instructions from the user. Specifically, a keyboard, a mouse, and various types of switches, for example, may be used as the console input interface 105. The console input interface 105 outputs signals corresponding to various instructions to the processing circuitry 101 via a bus. The console input interface 105 may be provided at the gantry apparatus 10, not only at the console 100.

The memory 107 is a storage device such as an HDD, an SSD, or an integrated circuit storage unit, etc., configured to store various kinds of information. The memory 107 may be a drive, etc. configured to read and write various kinds of information with respect to a portable storage medium such as a CD-ROM drive, a DVD drive, or a flash memory, etc. The memory 107 stores data of, for example, a CT image and a display image. Furthermore, the memory 107 stores a control program and the like according to the present embodiment.

The encoder 29 is a rotary-type absolute encoder or a linear-type absolute encoder, for example. The gantry 11 is an approximately cylindrical-shaped structure having the bore 15 along the vertical direction. As shown in FIG. 1, the gantry 11 accommodates an X-ray tube 17 and an X-ray detector 19 which face each other with the bore 15 therebetween. The gantry control circuitry 25 may be accommodated in the gantry 11.

The columns 13 are a base (stand) for supporting the gantry 11 at an interval from the floor surface. The column 13 has a columnar shape such as a cylindrical shape or prismatic shape. The column 13 is formed from, for example, a material chosen as appropriate, such as a plastic or metal. The column 13 is attached to the side surface portion of the gantry 11, for example. Typically, the columns 13 are provided on the side surface of the gantry 11, facing each other. In other words, the plurality of columns 13 facing each other with the gantry 11 therebetween are placed with one end of the bore 15 facing the floor surface to support the gantry 11 movably along the vertical direction. However, the present embodiment is not limited thereto. For example, three or more columns 13 may be provided on the side surface of the gantry 11.

The columns 13 are not limited to those supporting the gantry 11 in such a manner that the central axis A1 is located in the vertical direction with respect to the floor surface. In other words, the columns 13 may be configured to support the gantry 11 rotatably around the horizontal axis (referred to as the tilt axis hereinafter) which is in parallel with the floor surface. In this case the columns 13 and the gantry 11 are preferably connected to each other through bearings so that the gantry body 11 can rotate around the tilt axis. Thus, the imaging for a subject in a standing state, a sitting state, and a lying position can be achieved by one gantry apparatus 10.

As shown in FIG. 1, the gantry drive motors 27 for driving the gantry 11 in the vertical direction are respectively accommodated in the columns 13. The gantry drive motor 27 generates power to drive the gantry 11 with respect to the vertical direction according to the control from gantry control circuitry 25. Specifically, the gantry drive motors 27 generates power by being driven at a rotational speed corresponding to a duty ratio or the like of a driving signal from the gantry control circuitry 25. Upon receiving power from the gantry drive motors 27, the columns 13 support the gantry 11 so that the gantry 11 can move in the vertical direction with respect to the columns 13. In other words, the plurality of gantry drive motors 27 move the gantry 11 in the vertical direction under the control of the gantry control circuitry 25. For example, the gantry drive motors 27 move the gantry 11 under the control of the gantry control circuitry 25 at a speed in accordance with an operator's instruction that is input through the console input interface 105 or the gantry input interface 28. The speed in accordance with an operator's instruction is a first speed at which the gantry 11 is moved to the proximity of an imaging target region of a subject, and a second speed at which the position of the gantry 11 is adjusted in accordance with the imaging target region. At this time, the first speed is faster than the second speed. The speed in accordance with an operator's instruction is not limited to those two speeds, and may be three or more different speeds. The gantry drive motors 27 are achieved by a motor, such as a servo motor, etc., for example. The gantry drive motors 27 are not limited to those being installed in the column 13; they may be accommodated in the gantry 11, for example.

The gantry input interface 28 (an operation unit) is provided on at least one column 13. The gantry input interface 28 is achieved by a switch button, a touch pad through which an input operation is carried out by touching an operation surface, and a touch panel display with an integrated display screen and touch pad, etc. The gantry input interface 28 converts an input operation received from an operator into electric signals, and outputs the electric signals to the gantry control circuit 25. The gantry input interface 28 accepts an instruction to freely move the gantry 11 in the vertical direction at a speed in accordance with an operator's instruction. When the gantry 11 is interlocked by the gantry drive motors 27, the gantry input interface 28 accepts a release instruction to release the interlocking state of the gantry 11. The interlocking state of the gantry 11 is a state where the gantry 11 cannot be moved unless a release instruction is made. The gantry input interface 28 outputs the release instruction to the gantry control circuitry 25. After accepting the release instruction, the gantry input interface 28 accepts a movement instruction to move (raise) the gantry 11 toward a reference position (home position), which will be described later. The gantry input interface 28 may display display modes, such as flashing and lighting, in accordance with a determination result by the determination function 251.

A position detector is provided at each of the plurality of columns 13. The position detector detects a support position where the gantry 11 is supported by the column 13. The support position is, for example, a position where the gantry 11 and each column 13 are in contact through supporting members (not shown). The supporting members are linear motion bearings and a linear guide, for example. The position detector outputs information regarding the support position to the gantry control circuitry 25. The position detector is achieved by, for example, an encoder 29 and a gantry detection sensor 30. As a modification of the present embodiment, the position detector may be achieved by either one of the encoder 29 or the gantry detection sensor 30.

If the encoder 29 is a rotary-type absolute encoder, for example, it has a slit disk (not shown) and an optical detection unit (not shown), for example. A slit disk is provided at the motor rotation axis of the gantry drive motor 27, for example. The slit disk has a slit indicative of an angle and a rotation direction of the motor rotation axis. A detection unit has a light emitting source and a light receiving element (not shown). The detection unit receives a light transmitted through the slit of the slit disk to generate an encoder value in accordance with a number of times of rotation and a rotation direction. The generated encoder value corresponds to the number of times of rotation of the motor rotation axis of the gantry drive motor 27 in the movement of the gantry 11 along the vertical direction. In other words, the encoder value corresponds to a distance of the movement of the gantry 11 along with the motor rotation. The encoder 29 outputs the generated encoder value to the gantry control circuitry 25 as information regarding the support position.

As another example, if the encoder 29 is a linear-type absolute encoder, it has a scale and a detection head (not shown). A scale is provided at each of the columns 13. A detection head is provided at the gantry 11. The detection head reads the scale based on a given method, such as an optical method or a magnetic method. The encoder 29 reads the scale to detect the support position of the gantry 11 in the column 13. The encoder 29 outputs the encoder value generated by reading the scale to the gantry control circuitry 25 as information regarding the support position.

The gantry detection sensors 30 are respectively provided at the plurality of columns 13. Specifically, the gantry detection sensors 30 are provided facing each other in parallel, with a space between the plurality of columns 13, in other words, with a space in which the gantry 11 is moved in the vertical direction therebetween. In other words, in the plurality of columns 13, the gantry detection sensors 30 provided horizontally facing each other are located on a horizontal plane. The gantry detection sensor 30 has a predetermined detection region in this horizontal plane. The gantry detection sensor 30 detects whether or not at least part of the gantry 11 reaches the detection region in the horizontal plane. In other words, the gantry detection sensor 30 detects a timing when part of the gantry 11 reaches the detection region. The gantry detection sensor 30 outputs the timing of the detection of part of the gantry 11 to the gantry control circuitry 25 as information regarding the support position. The horizontal plane is not limited to one surface; there may be a plurality of planes. In this case, a plurality of gantry detection sensors 30 are provided along the vertical direction in each of the plurality of columns 13.

The gantry detection sensor 30 is achieved by a photo sensor, for example. The photo sensor may be any type of photo sensors, such as a transmission photo sensor or a reflective photo sensor. The photo sensor has a light receiving element, such as a photo transistor, a photo diode, or a photo IC, and a light emitting element, such as an infrared LED. The light emitting element constantly emits a light, such as infrared light.

If the gantry detection sensor 30 is a transmission photo sensor, a sensor dog (jig) that can pass between the light receiving element and the light emitting element when the gantry 11 is moved in the approximately vertical direction is provided in the gantry 11. In this case, the transmission photo sensor detects timing when the sensor dog passes between the light receiving element and the light emitting element. If the gantry detection sensor 30 is a reflective photo sensor, upon moving of part of the gantry 11 to the detection region, the reflective photo sensor receives infrared light reflected by the part of the gantry 11, and detects timing of the reception. The gantry detection sensor 30 is not limited to the photo sensor; it may be any sensor, such as a ultrasonic sensor.

The position detector may detect misalignment information indicative of a horizontal level of the gantry 11, in other words, a degree of the misalignment between the plurality of support positions. In this case, the position detector is, for example, an acceleration sensor or a level that is implemented in the gantry 11. The position detector may be any type of known detectors, as long as the detector can detect a horizontal level of the gantry 11, in other words, a parallel level of the gantry with respect to the floor surface. The acceleration sensor detects a tilt of the gantry 11 with respect to the vertical direction. The level has a bubble tube, for example. The level detects the tilt of the gantry 11 with respect to the horizontal plane in accordance with the position of a bubble in the bubble tube. The position detector outputs the tilt of the gantry to the gantry control circuitry 25.

In each of the columns 13, an upper limit sensor (not shown), which detects at least part of the gantry 11 at an upper limit of the movement of the gantry 11, is provided. If the upper limit sensor provided in the column 13 detects part of the gantry 11, the gantry drive motor 27 of this column stops the movement of the gantry 11. At this time, in the column 13 where the upper limit sensor by which part of the gantry 11 has been detected is provided, the support position of the gantry 11 is an upper limit position that corresponds to a position of the upper limit sensor which detects part of the gantry 11. When all of the support positions related to the gantry 11 reach the upper limit position, the encoder value is reset to zero under the control of the gantry control circuit 25. In the gantry 11 which has arrived at the upper limit position, the surface facing the floor surface corresponds to a reference position.

In each of the columns 13, a lower limit sensor which detects part of the gantry 11 in a lower limit of the movement of the gantry 11 is provided. If the lower limit sensor provided in the column 13 detects part of the gantry 11, the gantry drive motor 27 of this column stops the movement of the gantry 11. At this time, in the column 13 where the lower limit sensor by which part of the gantry 11 has been detected is provided, the support position of the gantry 11 is an lower limit position that corresponds to a position of the lower limit sensor which detects the gantry 11. The upper limit sensor and the lower limit sensor are achieved by the aforementioned photo sensors, etc.

The gantry control circuitry 25 that achieves the determination function 251 achieves a function of determining whether or not the gantry 11 can move in the vertical direction, depending on a degree of a misalignment between a plurality of support positions (misalignment information). The gantry control circuitry 25 stores a first threshold and a second threshold used by the determination function 251 in a self memory. The first threshold and the second threshold are thresholds for distinguishing a misalignment depending on a degree of the misalignment. Suppose the first threshold is smaller than the second threshold. The first threshold and the second threshold are used by the determination function 251. The thresholds are not limited to those thresholds; they may be set in accordance with control of the movement of the gantry 11.

The gantry control circuitry 25 that achieves the determination function 251 determines whether or not the gantry 11 can move in the vertical direction based on information regarding the support positions. In other words, the gantry control circuitry 25 determines whether or not the gantry 11 can move along the vertical direction based on information regarding a misalignment between the plurality of support positions. Specifically, the gantry control circuitry 25 calculates, as misalignment information, a misalignment between the support positions with respect to the vertical direction, based on information regarding the support positions. For example, if the information regarding the support positions is encoder values, the gantry control circuitry 25 calculates, as a misalignment (misalignment information) an absolute value of a difference between a plurality of encoder values that are respectively output from the plurality of encoders 29 provided in the plurality of columns 13. If the information regarding the support positions is timing, the gantry control circuitry 25 calculates, as a misalignment (misalignment information) an absolute value of a difference between a plurality of timings (times) that are respectively obtained at the plurality of gantry detection sensors 30 included in one horizontal plane provided in each of the plurality of columns 13. The processing circuitry 25 that achieves the determination function 251 corresponds to a determination unit.

If an acceleration sensor, a level, or the like is used as the position detector, the gantry control circuitry 25 calculates misalignment information using a distance between the columns 13 and a tilt of the gantry 11. Specifically, the gantry control circuitry 25 calculates a misalignment between the supporting positions as misalignment information by multiplying a tangent of an angle indicative of the tilt of the gantry 11 by the distance between the columns 13. If the tilt of the gantry 11 is used as the misalignment information instead of misalignment information between the support positions, an output from the acceleration sensor or the level used as the position detector is misalignment information; thus, it becomes unnecessary to calculate misalignment information.

The gantry control circuitry 25 that achieves the determination function 251 determines whether or not the misalignment is smaller than the first threshold. If the misalignment is smaller than the first threshold, the gantry control circuitry 25 controls the gantry drive motors 27 so as to continue the movement of the gantry 11.

The gantry control circuitry 25 that achieves the determination function 251 determines whether or not a misalignment is included in a range defined by the first threshold and the second threshold. The range is defined to be, for example, equal to or greater than the first threshold and smaller than the second threshold. In addition, the gantry control circuitry 25 determines whether or not imaging for a subject is in progress. If a misalignment is included in the range and imaging is not in progress, the gantry control circuitry 25 controls the gantry drive motors 27 so as to eliminate the misalignment. Specifically, the gantry drive motor 27 changes a speed of moving the support positions, and moves the gantry 11 to eliminate the misalignment. For example, the gantry control circuitry 25 controls the gantry drive motors 27 in such a manner that the speed of the gantry 11 with respect to a column having a support position closer to the floor surface among the plurality of support positions detected by the position detector is set to be slower than the speed of the gantry 11 with respect to a column having a support position further from the floor surface among the plurality of support positions. The plurality of support positions are the positions where the gantry 11 is respectively in contact with the plurality of columns 13 through supporting members. The gantry control circuitry 25 may control the gantry drive motors 27 in such a manner that the speed of the gantry 11 with respect to a column having a support position further from the floor surface among the plurality of support positions detected by the position detector is set to be faster than the speed of the gantry 11 with respect to a column having a support position closer to the floor surface among the plurality of support positions. The control of the gantry drive motors 27 by the gantry control circuitry 25 may be performed by a combination of the above-described two types of controls. If the gantry control circuitry 25 determines that a misalignment is included in the range, the gantry control circuitry 25 causes the memory 107 to store position misalignment information including a time of occurrence of the misalignment (time and date, etc.) and the misalignment as a log related to the occurrence of the misalignment.

The gantry control circuitry 25 that achieves the determination function 251 determines whether or not the calculated misalignment (misalignment information) is greater than the second threshold. If the misalignment is greater than the second threshold, the gantry control circuitry 25 determines that the movement of the gantry 11 is impractical. In this case, the gantry control circuitry 25 controls the plurality of gantry drive motors 27 to stop the movement of the gantry 11. Subsequently, the gantry control circuitry 25 performs interlocking control for the plurality of gantry drive motors 27, the gantry input interface 28, and the console input interface 105. Specifically, the gantry control circuitry 25 controls the plurality of gantry drive motors 27 to interlock the gantry 11 after stopping the movement of the gantry 11. If the misalignment exceeds the second threshold, the gantry control circuitry 25 controls the console input interface 105 and the gantry input interface 28 in such a manner that an instruction to move the gantry 11 is not accepted from the console input interface 105 and the gantry input interface 28. At this time, at the console input interface 105, acceptance of an instruction to move the gantry 11 is disabled by the control of the gantry control circuitry 25.

In response to the interlocking control, the gantry control circuitry 25 that achieves the determination function 251 controls the display 103 to notify an operator of a warning regarding the misalignment in the form of a message, for example. A warning regarding the misalignment (misalignment information) is notified (displayed) to the operator by the display 103 in the form of, for example, a message, in response to the determination made by the determination function 251 that the movement of the gantry 11 is impractical. Furthermore, the gantry control circuitry 25 that achieves the determination function 251 reads the position misalignment information from the memory 107. Subsequently, the gantry control circuitry 25 transmits the information regarding the warning through a network (not shown), along with the read position misalignment information, to a terminal at a service center related to the present medical image diagnostic apparatus. Thus, a service person who is stationed in the service center is able to ascertain the occurrence of a misalignment and a point in time when a past misalignment has occurred. Herein, the gantry control circuitry 25 may control the gantry input interface 28 to display the display modes, such as flashing and lighting. The gantry control circuitry 25 controls a speaker (not shown) that is placed in a CT imaging room or a control room to notify an operator of a warning regarding the misalignment in the form of a warning sound.

After carrying out the interlocking control, the processing circuitry 25 controls the gantry input interface 28 so as to accept a release instruction. In response to an input of a release instruction through the gantry input interface 28, the gantry control circuitry 25 controls the gantry input interface 28 so as to accept a movement instruction. In response to an input of a movement instruction, the gantry control circuitry 25 controls the plurality of gantry drive motors 27 so as to move the gantry 11 to the reference position at the second speed. In other words, the gantry drive motors 27 move the gantry 11 to the reference position at a slower speed in accordance with the movement instruction that is input after the release instruction. When the gantry 11 reaches the reference position, the gantry control circuitry 25 releases various interlockings.

(Operation)

Figure 2:
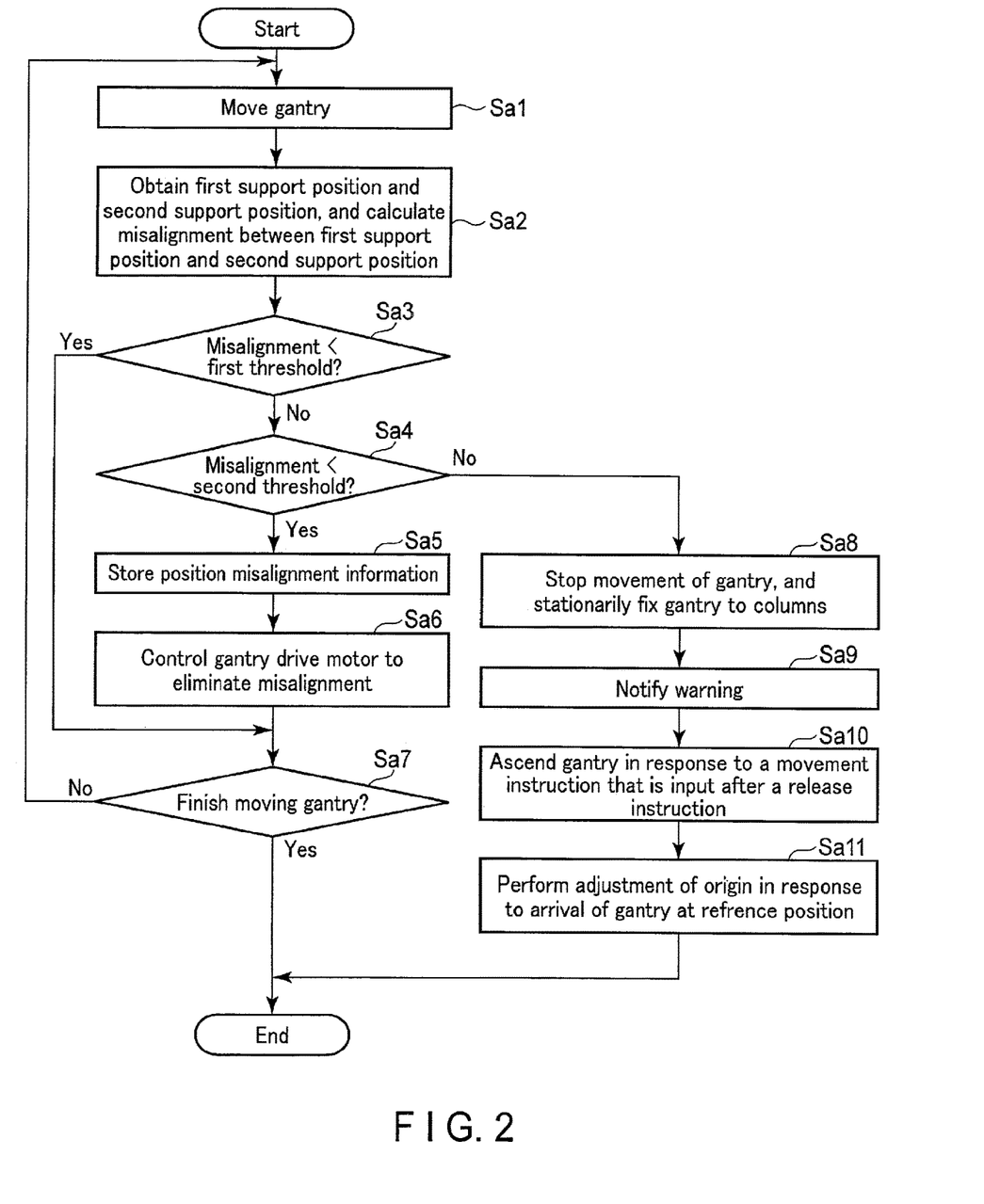
FIG. 2 is a flowchart showing an example of processing related to a determination function according to the present embodiment.

In the following, the processing of the determination function 251 in the present embodiment will be explained. FIG. 2 is a flowchart showing an example of the processing of the determination function 251. In the following, to make the description more specific, assume the columns 13 are provided on the side surface of the gantry 11, and the columns 13 constitute a pair that is symmetrically placed with respect to the gantry 11 (hereinafter, the left column and the right column). Also, assume the gantry detection sensors 30 are provided at each of the left column and the right column on each of four horizontal planes. In addition, assume the gantry 11 before carrying out the processing is placed at a reference position as an initial position.

(Step Sa1)

The gantry 11 is moved from the reference position toward the floor surface by an operator's instruction that is input through the console input interface 105 or the gantry input interface 28. Specifically, the gantry control circuitry 25 controls the gantry drive motor located in the left column and the gantry drive motor located in the right column in accordance with an operator's instruction. The gantry 11 is driven by these gantry drive motors to descend from the reference position at a first speed.

(Step Sa2)

An encoder value that is output from the encoder located in the left column is obtained as a support position in the left column (hereinafter, a first support position). In addition, an encoder value that is output from the encoder located in the right column is obtained as a support position in the right column (hereinafter, a second support position). If part of the gantry 11 passes the detection region of the gantry detection sensors 30 included in one horizontal plane, the timing of detection output from the gantry detection sensor located in the left column is obtained as the first support position, and the timing of detection output from the gantry detection sensor located in the right column is obtained as the second support position. A misalignment is calculated based on a difference between the first support position and the second support position. In other words, the comparison between the first support position and the second support position (calculation of the misalignment) is constantly performed throughout the movement of the gantry 11.

(Step Sa3)

The misalignment is compared with the first threshold by the determination function 251. If the misalignment is smaller than the first threshold (Yes in step Sa3), the processing in step Sa1 is performed. If the misalignment is equal to or greater than the first threshold (No in step Sa3), the processing in step Sa4 is performed.

(Step Sa4)

The misalignment is compared with the second threshold by the determination function 251. If the misalignment is smaller than the second threshold (Yes in step Sa4), the processing in step Sa5 is performed as long as imaging for a subject is not in progress. If the misalignment is equal to or greater than the second threshold (No in step Sa4), the processing in step Sa8 is performed.

Figure 3:
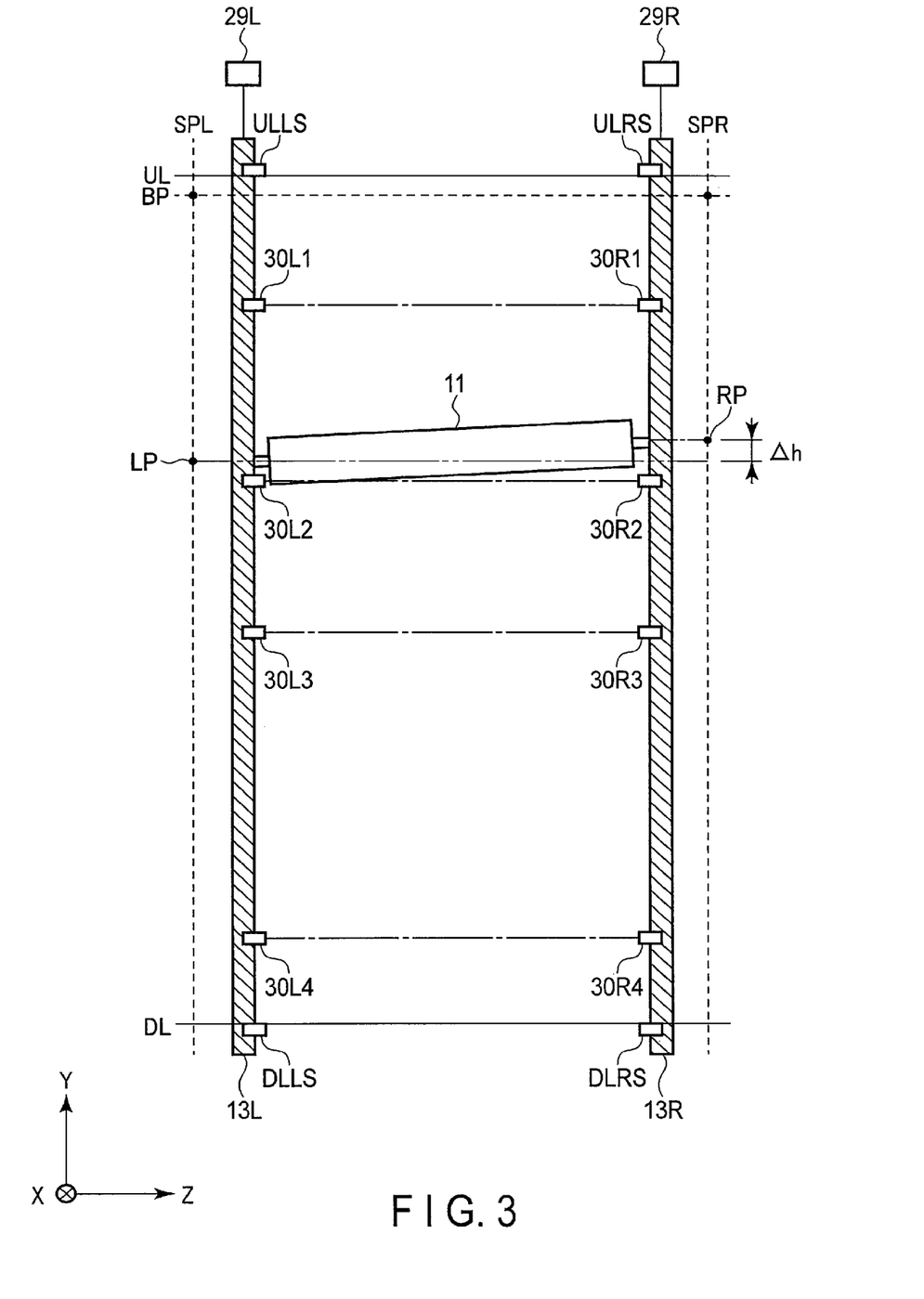
FIG. 3 is a diagram explaining a misalignment in the present embodiment.

FIG. 3 is a diagram explaining a misalignment. FIG. 3 is a diagram of the gantry apparatus 10 shown in FIG. 1, viewed from X-axis direction. In the left column 13L, as shown in FIG. 3, from the top to the bottom, a left encoder 29L, an upper limit sensor OILS, four gantry detection sensors 30L1, 30L2, 30L3, and 30L4 located in four different horizontal planes corresponding to four different positions along Y-axis direction, and a lower limit sensor DLLS are provided. In the right column 13R, from the top to the bottom, a right encoder 29R, an upper limit sensor ULRS, four gantry detection sensors 30R1, 30R2, 30R3, and 30R4 located in four different horizontal planes corresponding to four different positions along the Y-axis direction, and a lower limit sensor DLRS are provided. The UL in FIG. 3 indicates the upper limit line for detection of the gantry 11 by the upper limit sensors ULLS and ULRS, and corresponds to the reference position BP which is indicated by a dashed line. When the gantry 11 is located on the upper limit detection line, the encoder value is zero. The DL in FIG. 3 indicates the lower limit line for detection of the gantry 11 by the lower limit sensors DLLS and DLRS. The dashed line SPL on the left side of the left column 13L is a number line indicative of an encoder value that is output from the left encoder 29L located in the left column 13L. The dashed line SPR on the right side of the right column 13R is a number line indicative of an encoder value that is output from the right encoder 29R located in the right column 13R. The LP in FIG. 3 indicates a first support position, and the RP indicates a second support position.

The misalignment is indicated by $\Delta h$ in FIG. 3. The misalignment $\Delta h$, which is calculated in step Sa2, corresponds to an absolute value |LP−RP| of a difference between the first support position LP and the second support position RP. The misalignment that is output from the gantry detection sensors 30 is calculated by the gantry control circuitry 25 based on a difference between timings of detection of part of the gantry 11 in a pair of the gantry detection sensors included in the same horizontal plane (i.e., 30L1 and 30R1; 30L2 and 30R2; 30L3 and 30R3; and 30L4 and 30R4).

If the misalignment $\Delta h$ is smaller than the first threshold ($\Delta h$<first threshold), the gantry 11 further descends along Y axis. If the misalignment $\Delta h$ is included in a range equal to or greater than the first threshold and smaller than the second threshold (first threshold≤$\Delta h$<second threshold) and imaging for a subject is not in progress, the processing in step Sa5 is performed. If the misalignment $\Delta h$ is equal to or greater than the second threshold ($\Delta h$≥second threshold), the processing in step Sa8 is performed.

(Step Sa5)

The position misalignment information that includes a misalignment (misalignment information) and a point in time of the occurrence of the misalignment (time and date, etc.) is stored in the memory 107 as a log regarding the misalignment.

(Step Sa6)

If imaging for a subject is not in progress, in order to eliminate the misalignment $\Delta h$, the gantry drive motor located in the left column 13L and the gantry drive motor located in the right column 13R are controlled by the gantry control circuitry 25. As shown in FIG. 3, if the first support position LP in the gantry 11 is closer to the floor surface than the second support position RP is, the gantry drive motor located in the left column 13L is controlled so as to slow the speed of moving the first support position in the left column 13L. This control is performed until the misalignment Δh becomes smaller than the first threshold. By this control, the misalignment Δh included in the range equal to or greater than the first threshold and smaller than the second threshold is reduced to be smaller than the first threshold.

(Step Sa7)

If the movement of the gantry 11 is not finished (No in step Sa7), the processing after step Sa1 is repeated. If the movement of the gantry 11 is finished (Yes in step Sa7), the processing is finished.

(Step Sa8)

If the misalignment Δh is equal to or greater than the second threshold, the movement of the gantry 11 is stopped, and the gantry 11 is interlocked with the left column 13L and the right column 13R. In the state shown in FIG. 3, if the misalignment Δh becomes equal to or greater than the second threshold, the gantry 11 is interlocked at the first support position LP and the second support position RP. In addition, by performing the interlock control, the input of an instruction to move the gantry 11 through the console input interface 105 and the gantry input interface 28 is disabled. In addition, an input of a release instruction is enabled in the gantry input interface 28.

(Step Sa9)

When the interlock control is performed, a warning of the misalignment is displayed on the display 103 in the form of, for example, text. In addition, if the position misalignment information is stored in the memory 107, the position misalignment information is transmitted to a terminal device at the service center along with the warning of the misalignment.

(Step Sa10)

When a release instruction is input through the gantry input interface 28, an input of a movement instruction in the gantry input interface 28 is enabled. When a movement instruction is input at the gantry input interface 28, the gantry 11 ascends toward the reference position BP under operation restrictions. Operation restrictions are, for example, to allow only the ascending operation at a low speed (a second speed) for the movement of the gantry 11. A subject can be thereby evacuated.

(Step Sa11)

In response to arrival of the gantry 11 at the reference position BP, adjustment of origin is performed. Specifically, by inputting a movement instruction under the state shown in FIG. 3, part of the gantry 11 in proximity to the right column 13R arrives at the upper limit detection line UL earlier than part of the gantry 11 in the proximity of the left column 13L arrives. At this time, the gantry drive motor located in the right column 13R stops the movement of the gantry 11 in the right column 13R. At this time, the second support position RP shown in FIG. 3 is the reference position BP. In response to stopping the movement of the gantry 11 by the gantry drive motor located in the right column 13R, the encoder value of the right encoder 29R in the right column 13R becomes zero. Subsequently, part of the gantry 11 in proximity to the left column 13L arrives at the upper limit detection line UL. At this time, the gantry drive motor located in the left column 13L stops the movement of the gantry 11 in the left column 13L. At this time, the first support position LP shown in FIG. 3 is the reference position BP. In response to stopping the movement of the gantry 11 by the gantry drive motor located in the left column 13L, the encoder value of the left encoder 29L becomes zero.

By the processing in this step, the first support position LP and the second support position RP in the gantry 11 match the reference position BP. In other words, the misalignment Δh is thus eliminated. Furthermore, the encoder values in the right encoder 29R and the left encoder 29L are reset to zero, and the adjustment of the origin is completed in this step.

According to the above-described configuration, the following advantageous effects can be obtained.

According to the medical image diagnostic apparatuses of the present embodiment, in a plurality of columns that movably support the gantry 11 along the vertical direction, with one end of the bore 15 along the vertical direction facing the floor surface and the gantry 11 having the bore 15 being interposed between the columns, it is possible to detect a plurality of support positions at which the gantry 11 is supported by the plurality of columns, and to determine whether the movement of the gantry 11 along the vertical direction is possible or not. Specifically, according to the medical image diagnostic apparatus, if a misalignment Δh between the support positions in the vertical direction exceeds the second threshold, it is determined that the movement of the gantry 11 is impractical, and in response to the determination, the movement of the gantry 11 is stopped and the gantry 11 is interlocked. Furthermore, according to the present medical image diagnostic apparatus, it is possible to notify an operator of a warning regarding the misalignment in response to the determination that the movement of the gantry 11 is impractical. Furthermore, according to the medical image diagnostic apparatus, in the gantry input interface 28, a release instruction to release the interlock of the gantry 11 in a state where the gantry 11 is interlocked, and a movement instruction to move the gantry 11 can be input, and in response to a movement instruction that is input after a release instruction, the gantry 11 can be moved to the reference position BP at a second speed.

As described above, according to the present medical diagnostic apparatus, encoder values of the encoders 29 are constantly compared during the movement of the gantry 11, and if there is a misalignment equal to or greater than a second threshold, which is detected as an error, the interlock control is performed to immediately stop the movement operation of the gantry 11. Thus, if an error is detected before imaging for a subject starts, the process does not proceed to imaging so that an influence of the misalignment to a reconstruction image can be reduced. Furthermore, when an error is detected, an error message is displayed on the display 103 of the console 100 to notify an operator of a warning. Furthermore, after releasing the interlock control, the gantry 11 ascends at a low speed to adjust the origin by setting encoder values to zero when the gantry 11 arrives at the upper limit sensors ULLS and ULRS. The misalignment Δh can be thereby corrected, and the encoder values can be returned. At this time, according to the present medical image diagnostic apparatus, it is possible to avoid risks such as catching a patient between the column and the gantry at the time of return of the gantry by introducing operation restrictions, in other words, by allowing only an ascending operation at a low speed, and to evacuate a subject safely.

According to the medical image diagnostic apparatus in the present embodiment, the encoder value that is output from the encoder 29 and/or the timing when part of gantry 11 passes a region detection of the gantry detection sensor 30 is constantly compared during the movement of the gantry 11, and it is determined whether or not a misalignment is included in a range defined by the first threshold which is smaller than the second threshold and the second threshold, and if it is determined a misalignment is included in the range and imaging for a subject that is not in progress, the moving speed of each of the plurality of support positions is changed so as to eliminate the misalignment Δh, and the gantry 11 is moved. In addition, according to the present medical image diagnostic apparatus, if it is determined that the misalignment Δh is included in the range, position misalignment information that includes a point in time when the misalignment Δh occurs and the misalignment Δh can be stored.

Thus, according to the present medical image diagnostic apparatus, if a misalignment Δh is included in the range defined by the first and second thresholds, the misalignment Δh can be automatically corrected. By correcting the misalignment Δh, the occurrence of the misalignment can be prevented at the time of adjusting an imaging position before imaging begins, and an influence to a reconstruction image can be reduced when movement of a subject's joints is observed when a standing or sitting subject's weight is applied. It is thus possible to prevent harm to a subject in advance, such as unnecessary exposure to X-rays due to re-imaging. In addition, according to the present medical image diagnostic apparatus, position misalignment information can be stored as a log as a warning for occurrences of a misalignment larger than the second threshold. It is thereby possible for service personnel to ascertain and estimate progress of a misalignment Δh using the position misalignment information, and to utilize the position misalignment information for analysis, etc. of causes and trends of occurrences of misalignment Δh. Thus the occurrence of misalignment Δh can be reduced.

Modification

A difference from the present embodiment is to use loads on servo motors corresponding to the gantry drive motors 27 during the movement of the gantry 11, instead of the encoders 29 in the position detectors, in order to determine whether the movement of the gantry 11 in the vertical direction is possible or not.

A load detector is arranged adjacently to each of the gantry drive motors 27 shown in FIG. 1. Each load detector may be accommodated in the gantry drive motor 27. A plurality of load detectors detect a plurality of loads related to the movement of the gantry 11 in the servo motors corresponding to the gantry drive motors 27. The load detector is achieved by a torque sensor (torque detector) that detects torque of a rotation axis of the servo motor. Each of the plurality of load detectors outputs information regarding a load detected in each of the gantry drive motors 27 to the gantry control circuitry 25.

The gantry control circuitry 25 which achieves the determination function 251 determines whether the movement of the gantry 11 in the vertical direction is possible or not based on the information regarding the plurality of loads that are respectively output from the plurality of load detectors. Specifically, the gantry control circuitry 25 compares each of a plurality of loads with a load-related threshold (hereinafter, a load threshold) at each of a plurality of points in time during the movement of the gantry 11. A load threshold is stored in a memory, etc. in the gantry control circuitry 25, for example, and is a threshold corresponding to the above-described second threshold. The operation in the present modification corresponding to FIG. 2 is as described below.

In step Sa2, a load is detected at each of the gantry drive motors 27. Subsequently, in step Sa3, each of the plurality of loads is compared with a load threshold. If the plurality of loads are smaller than the load threshold, the processing in step Sa7 is performed. If at least one of the plurality of loads is equal to or greater than the load threshold, the processing from step Sa8 to step 10 is performed.

According to the above-described configuration, the following advantageous effects can be obtained in addition to the advantageous effects described in the present embodiment.

According to the medical image diagnostic apparatuses of the present modification, in a plurality of gantry drive motors 27 located in a plurality of columns that movably support the gantry 11 along the vertical direction, with one end of the bore 15 along the vertical direction facing the floor surface and the gantry 11 having the bore 15 interposed between the columns, it is possible to detect a plurality of loads related to the movement of the gantry 11, and to determine whether or not the movement of the gantry 11 along the vertical direction is possible, based on the information related to the loads. Thus, according to the medical image diagnostic apparatus, advantageous effects similar to those of the present embodiment can be obtained by using the load detectors, instead of the position detectors.

According to the medical image diagnostic apparatus according to the foregoing embodiment and modification, etc., harm to a subject and the present medical image diagnostic apparatus due to occurrence of a misalignment can be prevented, thereby improving safety measures. Thus, according to the present medical image diagnostic apparatus, imaging in a sitting state or in a standing state can be safely performed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
   a gantry having a bore along a vertical direction;
   a plurality of columns that movably support the gantry along the vertical direction, with one end of the bore facing a floor surface and the gantry being interposed between the plurality of columns;
   a plurality of gantry drive motors that move the gantry along the vertical direction;
   a plurality of position detectors that detect a plurality of support positions at which the gantry is supported in each of the plurality of columns; and
   gantry control circuitry that determines whether or not movement of the gantry along the vertical direction is possible, based on information regarding misalignment between the plurality of support positions.

2. The medical image diagnostic apparatus according to claim 1, wherein
   the gantry control circuitry determines the movement is impractical when the misalignment information between the plurality of support positions in the vertical direction exceeds a threshold, and the gantry drive motors stop the movement in response to a determination that the movement is impractical.

3. The medical image diagnostic apparatus according to claim 2, wherein
the gantry drive motors interlock the gantry after stopping the movement so that the gantry is not moved.

4. The medical image diagnostic apparatus according to claim 2, further comprising a display for notifying an operator of a warning regarding the misalignment information in response to the determination that the movement is impractical.

5. The medical image diagnostic apparatus according to claim 3, further comprising
a gantry input interface that is provided on at least one of the plurality of columns, that accepts a release instruction to release an interlock of the gantry in a state where the gantry is interlocked, and that accepts a movement instruction to move the gantry, wherein
the gantry drive motors ascend the gantry in accordance with the movement instruction that is input after the release instruction.

6. The medical image diagnostic apparatus according to claim 2, wherein
the gantry control circuitry determines whether or not the misalignment information is included in a range that is defined by the threshold and a small threshold smaller than the threshold, and
the gantry drive motors change a moving speed of the plurality of support positions so as to eliminate the misalignment information and moves the gantry, if it is determined that the misalignment information is included in the range and imaging for a subject is not in progress.

7. The medical image diagnostic apparatus according to claim 6, further comprising a memory that stores, when it is determined that the misalignment information is included in the range, position misalignment information including the misalignment information and a point in time when the misalignment information occurs.

8. The medical image diagnostic apparatus according to claim 1, wherein
the position detectors
are a plurality of encoders located in the plurality of columns, and/or a plurality of gantry detection sensors that are located at a position included in one horizontal plane in the plurality of columns and that detect whether or not part of the gantry arrives at a detection region in the horizontal plane,
output, if the position detectors are the plurality of encoders, encoder values to the gantry control circuitry as information related to the plurality of support positions, and
output, if the position detectors are the plurality of gantry detection sensors, timing of detecting part of the gantry to the gantry control circuitry as information related to the plurality of support positions.

9. A medical image diagnostic apparatus, comprising:
a gantry having a bore along a vertical direction;
a plurality of columns that movably support the gantry along the vertical direction, with one end of the bore facing a floor surface and the gantry being interposed between the plurality of columns;
a plurality of gantry drive motors that move the gantry along the vertical direction;
a plurality of load detectors that respectively detect a plurality of loads related to movement of the gantry in the gantry drive motor; and
gantry control circuitry that determines whether or not movement of the gantry along the vertical direction is possible based on load information regarding the plurality of loads.

* * * * *